United States Patent
Szypka et al.

(10) Patent No.: US 11,259,967 B2
(45) Date of Patent: Mar. 1, 2022

(54) ABSORBENT COMPOSITE

(71) Applicant: Principle Business Enterprises, Inc., Dunbridge, OH (US)

(72) Inventors: Andrew J. Szypka, Curtice, OH (US); Blake Miller, Temperance, MI (US); Joel Geerken, Waterville, OH (US); Steve Lazenby, Perrysburg, OH (US)

(73) Assignee: PRINCIPLE BUSINESS ENTERPRISES, INC., Dunbridge, OH (US)

(*) Notice: Subject to any disclaimer, the term of this patent is extended or adjusted under 35 U.S.C. 154(b) by 773 days.

(21) Appl. No.: 15/905,268

(22) Filed: Feb. 26, 2018

(65) Prior Publication Data

US 2018/0243139 A1    Aug. 30, 2018

Related U.S. Application Data

(60) Provisional application No. 62/463,024, filed on Feb. 24, 2017.

(51) Int. Cl.
*A61F 13/00* (2006.01)
*A61F 13/02* (2006.01)
(Continued)

(52) U.S. Cl.
CPC .. *A61F 13/00042* (2013.01); *A61F 13/00012* (2013.01); *A61F 13/00017* (2013.01);
(Continued)

(58) Field of Classification Search
CPC .............. A61F 13/00042; A61F 13/536; A61F 13/00012; A61F 13/00017; A61F 13/0209;
(Continued)

(56) References Cited

U.S. PATENT DOCUMENTS

| 3,817,827 A | 6/1974 | Benz | |
| 4,333,979 A * | 6/1982 | Sciaraffa | D04H 3/14 |
| | | | 428/179 |

(Continued)

FOREIGN PATENT DOCUMENTS

| EP | 0494112 A2 | 7/1992 | |
| WO | 2009019226 A2 | 2/2009 | |
| WO | WO-2012086374 A1 * | 6/2012 | ........... D21H 27/002 |

OTHER PUBLICATIONS

"WO2012086374_Machine Translation" is a machine translation of WO-2012086374-A1. (Year: 2012).*

*Primary Examiner* — Larissa Rowe Emrich
(74) *Attorney, Agent, or Firm* — Jacob M. Ward; Ward Law Office LLC (57) ABSTRACT

An absorbent composite includes a porous base layer, a core layer, and a superabsorbent laminate layer. The core layer has a fluff pulp layer and superabsorbent polymer particles. The core layer is disposed on the base layer. The superabsorbent laminate layer is disposed on the core layer. The base layer, the core layer, and the superabsorbent laminate layer are compressed together and embossed under heat and pressure to form a plurality of embossed depressions. The embossed depressions are arranged across a major surface area of the superabsorbent laminate layer. The embossed depressions extend through the composite from the superabsorbent laminate layer and into the core layer and the base layer. A thin, soft, and pliable absorbent composite suitable for a variety of applications including wound care is thereby provided.

19 Claims, 5 Drawing Sheets

(51) Int. Cl.
*A61F 13/536* (2006.01)
*A61F 13/53* (2006.01)
*A61F 13/51* (2006.01)
*A61L 15/28* (2006.01)
*A61L 15/60* (2006.01)

(52) U.S. Cl.
CPC .. *A61F 13/00068* (2013.01); *A61F 13/00995* (2013.01); *A61F 13/0209* (2013.01); *A61F 13/536* (2013.01); *A61L 15/28* (2013.01); *A61L 15/60* (2013.01); *A61F 13/00063* (2013.01); *A61F 2013/51078* (2013.01); *A61F 2013/530591* (2013.01)

(58) Field of Classification Search
CPC .......... A61F 13/00995; A61F 13/00068; A61F 13/00063; A61F 13/00029; A61F 2013/530591; A61F 2013/51078; A61F 2013/00327; A61F 2013/15382; A61F 2013/530007–530124; A61F 2013/530481–530496; A61F 2013/530547–530562; A61F 2013/53445; A61F 2013/5395; A61F 13/00987; A61F 13/15747; A61L 15/28; A61L 15/60
See application file for complete search history.

(56) References Cited

U.S. PATENT DOCUMENTS

| | | | |
|---|---|---|---|
| 4,559,050 A | 12/1985 | Iskra | |
| 4,605,402 A | 8/1986 | Iskra | |
| 4,610,678 A | 9/1986 | Weisman et al. | |
| 4,950,264 A * | 8/1990 | Osborn, III | A61F 13/15203 604/385.08 |
| 5,021,050 A | 6/1991 | Iskra | |
| 5,242,435 A * | 9/1993 | Murji | A61F 13/533 604/374 |
| 5,460,622 A * | 10/1995 | Dragoo | A61F 13/15203 604/358 |
| 5,466,232 A | 11/1995 | Cadieux et al. | |
| 5,582,603 A | 12/1996 | Difilippantonio et al. | |
| 5,637,106 A * | 6/1997 | Mitchell | A61F 13/536 604/368 |
| 5,741,241 A | 4/1998 | Guidotti et al. | |
| 5,827,255 A * | 10/1998 | Crainic | A61F 13/476 604/378 |
| 5,868,727 A * | 2/1999 | Barr | A61F 13/5616 604/387 |
| 7,166,094 B2 | 1/2007 | Glaug et al. | |
| 7,619,130 B2 | 11/2009 | Nielsen et al. | |
| 7,759,540 B2 | 7/2010 | Litvay et al. | |
| 8,672,905 B2 | 3/2014 | Riesinger | |
| 2003/0204178 A1 * | 10/2003 | Febo | A61F 13/47 604/367 |
| 2005/0177122 A1 * | 8/2005 | Berba | A61F 13/537 604/367 |
| 2005/0247419 A1 * | 11/2005 | Hamed | A61L 15/60 162/157.6 |
| 2011/0184365 A1 * | 7/2011 | Rottger | A61L 15/28 604/372 |
| 2012/0323195 A1 * | 12/2012 | Ehrnsperger | A61F 13/534 604/366 |
| 2013/0012902 A1 | 1/2013 | Rovaniemi | |
| 2015/0065974 A1 | 3/2015 | Michiels et al. | |
| 2015/0119837 A1 * | 4/2015 | Thompson, Jr. | A61L 15/26 604/369 |
| 2015/0216742 A1 * | 8/2015 | Johnson | A61F 13/8405 604/359 |
| 2015/0351976 A1 | 12/2015 | Viens et al. | |
| 2016/0278997 A1 | 9/2016 | Wright et al. | |
| 2017/0348166 A1 * | 12/2017 | Ebert | A61F 13/534 |

* cited by examiner

ABSORBENT COMPOSITE

CROSS-REFERENCE TO RELATED APPLICATIONS

This application claims the benefit of U.S. Provisional Application No. 62/463,024, filed on Feb. 24, 2017. The entire disclosure of the above application is hereby incorporated herein by reference.

FIELD

The disclosure generally relates to an absorbent product and, more particularly, to a disposable superabsorbent composite.

BACKGROUND

Currently, there are many disposable wound care bandages or dressings being sold in the U.S. and European wound care markets. All disposable wound care bandages utilize an absorbent core to absorb blood, exudate, or other fluids to ensure cleanliness and comfort for the patient. These bandages require as much absorbent ability as possible, which can be achieved through increased loadings of superabsorbent polymer.

Bandages require discreetness, softness, and pliability to ensure patient comfort. However, highly absorbent pads severely lack in this aspect. As the superabsorbent polymer loading increases, the discreetness, softness, and pliability of the overall bandage decreases. Also, the pads become thicker, bulkier, rougher to the touch and are unable to conform to the patient. This is a major flaw of conventional high-performance absorbent cores.

There becomes a trade-off of either a highly absorbent and efficient bandage, or a comfortable, soft, thin and inefficient bandage, which requires changes often. If both characteristics could be achieved, there would be improved performance, efficiency and patient comfort. Improvements for both customer and supplier would be observed.

Currently, the only way premium wound dressings can achieve a highly absorbent product is through the use of thick absorbent cores. Recent swings of the wound care market have desired a thinner, softer, and more pliable product. Other markets also desire thin, soft, and pliable superabsorbent products. This has been an ongoing issue where many absorbent core and airlaid manufacturers have not been able to achieve this high level of absorbency and thinness of product, due to conventional airlaid processes being unable to deposit high concentrations of superabsorbent polymers.

There is a continuing need for an absorbent composite that is thin, soft, and pliable, and yet can achieve a high level of absorbency. Desirably, the absorbent composite may be used for a variety of applications including for wound care, feminine care, protective underwear, incontinence pads and liners, diapers, and food pads.

SUMMARY

In concordance with the instant disclosure, an absorbent composite that is thin, soft, and pliable, and yet can achieve a high level of absorbency, and which may be used for a variety of applications including for wound care, feminine care, protective underwear, incontinence pads and liners, diapers, and food pad, is surprisingly discovered.

In one embodiment, an absorbent composite includes a porous base layer, an absorbent core layer, and a superabsorbent laminate layer. The core layer has a fluff pulp layer and superabsorbent polymer particles. The core layer is disposed on the base layer. The superabsorbent laminate layer is disposed on the core layer. The base layer, the core layer, and the superabsorbent laminate layer are compressed together and embossed under heat and pressure to form a plurality of embossed depressions. The embossed depressions are arranged across a major surface area of the superabsorbent laminate layer. The embossed depressions extend through the composite from the superabsorbent laminate layer and into the core layer and the base layer. A thin, soft, and pliable absorbent composite suitable for a variety of applications is thereby provided.

In another embodiment, a method for manufacturing an absorbent composite includes the steps of providing a porous base layer, and applying a fluff pulp layer to the base layer to form an absorbent core layer. The core layer also includes superabsorbent polymer particles. A superabsorbent laminate layer is then applied onto the core layer. The base layer, the core layer, and the superabsorbent laminate layer are compressed together under heat and pressure. The base layer, the core layer, and the superabsorbent laminate layer are also embossed to form a plurality of embossed depressions arranged across a major surface area of the superabsorbent laminate layer. The embossed depressions extend through the composite from the superabsorbent laminate layer and into the core layer and the base layer.

In yet another embodiment, the absorbent composite has a total thickness of between about 900 microns and about 1,500 microns.

In a further embodiment, the absorbent composite is suitable for use in wound care, feminine care, protective underwear, incontinence pads and liners, diapers, and food pads, among other applications.

In a particular embodiment, the absorbent composite is a disposable bandage for wound care. Specifically, it is a composite material having: a) a first layer of single-ply cellulosic tissue; b) a second layer of airlaid nonwoven fibers made from fluff pulp, which is disposed atop the first layer, and which can either have about 80 grams per square meter (gsm) superabsorbent polymer mixed with the fibers or laid down atop the fibers; and c) a third layer of a Gelok® core disposed atop the second layer. Gelok® core, commercially available from Gelok International in Dunbridge, Ohio, may be a double-pass laminate having three layers of single-ply cellulosic tissue with a 300 gsm of superabsorbent polymer particles sandwiched between, where 150 gsm layer of superabsorbent is between the first and second cellulosic tissue and another 150 gsm layer of superabsorbent is between the second and third cellulosic substrate layers (e.g., substrate/150 gsm SAP/substrate/150 gsm SAP/substrate). In other embodiments, the Gelok® core may be produced as a single-pass laminate with just the first and second cellulosic tissues, having about 200 gsm of the superabsorbent particles therebetween (e.g., substrate/200 gsm SAP/substrate). It should be appreciated that, in the case of the single pass laminate, certain manufacturing constraints may prohibit an application of greater than 200 gsm of the superabsorbent polymer particles between the tissues. In both cases, the entire assembly is compressed and embossed to form the final composite material.

Notably, there are no adhesives used to hold the composite together. Instead, the assembly is processed through a highly pressurized heated embossing unit with water or moisture applied in order for it to be held together through mechanical and hydrogen bonding forces. In use, the entire assembly is turned upside down so that the third layer of Gelok® core is the bottom-most layer for wicking and fluid reservoir, and the top two layers provide softness and pliability.

This assembly allows for the fabrication of one ultra-thin and ultra-absorbent core through the surprising use of incorporating two different technologies of air formed and superabsorbent laminate composites.

In an exemplary embodiment, the absorbent composite includes an air formed fluff composite with a superabsorbent laminate as the bottom substrate layer of the overall composite. The air formed fluff composite will be a range of 50 gsm to 150 gsm of untreated fiber formed onto a porous tissue and dosed with up to 80 gsm of superabsorbent polymer particles. The highly superabsorbent laminate will be produced off line as two layers of cellulose substrate, for example, airlaid, wetlaid, through-air dried cellulose, etc., with one layer of up to 300 gsm superabsorbent polymer particles in between the two layers of cellulose. The superabsorbent laminate will be processed during manufacturing of the core as the top substrate in order to allow fluff and superabsorbent polymer particles to be air formed onto a porous cellulose layer. The composite will be processed through a highly pressurized heated embossing unit with water or moisture applied and with a predetermined pattern configured for wicking and provision of a desired level of bonding (thickness) to achieve mechanical and hydrogen bonding of the components. During manufacturing of a finished product, the core will be rotated to have the superabsorbent laminate as the bottom most substrate of the product. This allows the superabsorbent laminate to act as a wicking layer and storage reservoir for fluids that are absorbed by the pad.

Although described herein primarily with respect to wound care, it should be understood that the absorbent composite of the present disclosure may be used in a variety of other applications where thinness, softness, pliability, and a high level of absorbency are desired, including for feminine care, protective underwear, incontinence pads and liners, diapers, and food pads, as non-limiting examples.

The present disclosure provides an absorbent composite capable of achieving large levels of absorbency while retaining critical intensive attributes such as softness, comfortability, drapability and thinness. The fluff found within the air formed core optimizes softness, comfortability, drapability while the superabsorbent laminate component optimizes the absorbency and thinness required in wound care bandage absorbent cores. Through the use of multiple layers of superabsorbent, up to 380 grams per square meter of superabsorbent may be achieved. The absorbent composite has excellent wicking ability and prevents gel-blocking from occurring due to the multiple substrate layers and fluff found throughout the product.

Multiple layers of superabsorbent also have potential to be replaced with alternative powdered chemicals and additives to optimize secondary properties of the product. Examples of this include use of hemostatic additives, active pharmaceutical ingredients, odor controlling agents, pH indicators, and the like. The layers of superabsorbent polymers can also be composed of various polymer types to optimize different attributes of the polymer. Potential polymer types include superabsorbent polymer specialized in blood absorption, quick fluid acquisition speeds, and high absorbency under load, as non-limiting examples.

The superabsorbent laminate found within the product helps optimize fluid acquisition, increasing absorbency efficiency and decreasing rewet values of the composite. The substrate layers found within the superabsorbent laminate are interchangeable with various wet laid, air laid, through air drying, etc. layers. Various substrates can be used to optimize key performance properties of the composite. Potential options include use of through air drying (TAD) for further improvements to fluid acquisition and wicking, or use of air laid for further softness and pliability, for example. One of the substrate layers found within the superabsorbent laminate can also be replaced with another superabsorbent laminate. This would allow for three layers of substrates and two layers of superabsorbent polymer in the laminate. The increased amount of raw materials would allow further depth and customization to the composite.

DRAWINGS

The above, as well as other advantages of the present disclosure, will become readily apparent to those skilled in the art from the following detailed description, particularly when considered in the light of the drawings described hereafter.

DETAILED DESCRIPTION

The following description is merely exemplary in nature and is not intended to limit the present disclosure, application, or uses. It should also be understood that throughout the drawings, corresponding reference numerals indicate like or corresponding parts and features. In respect of the methods disclosed, the order of the steps presented is exemplary in nature, and thus, is not necessary or critical unless otherwise disclosed.

Figure 1:
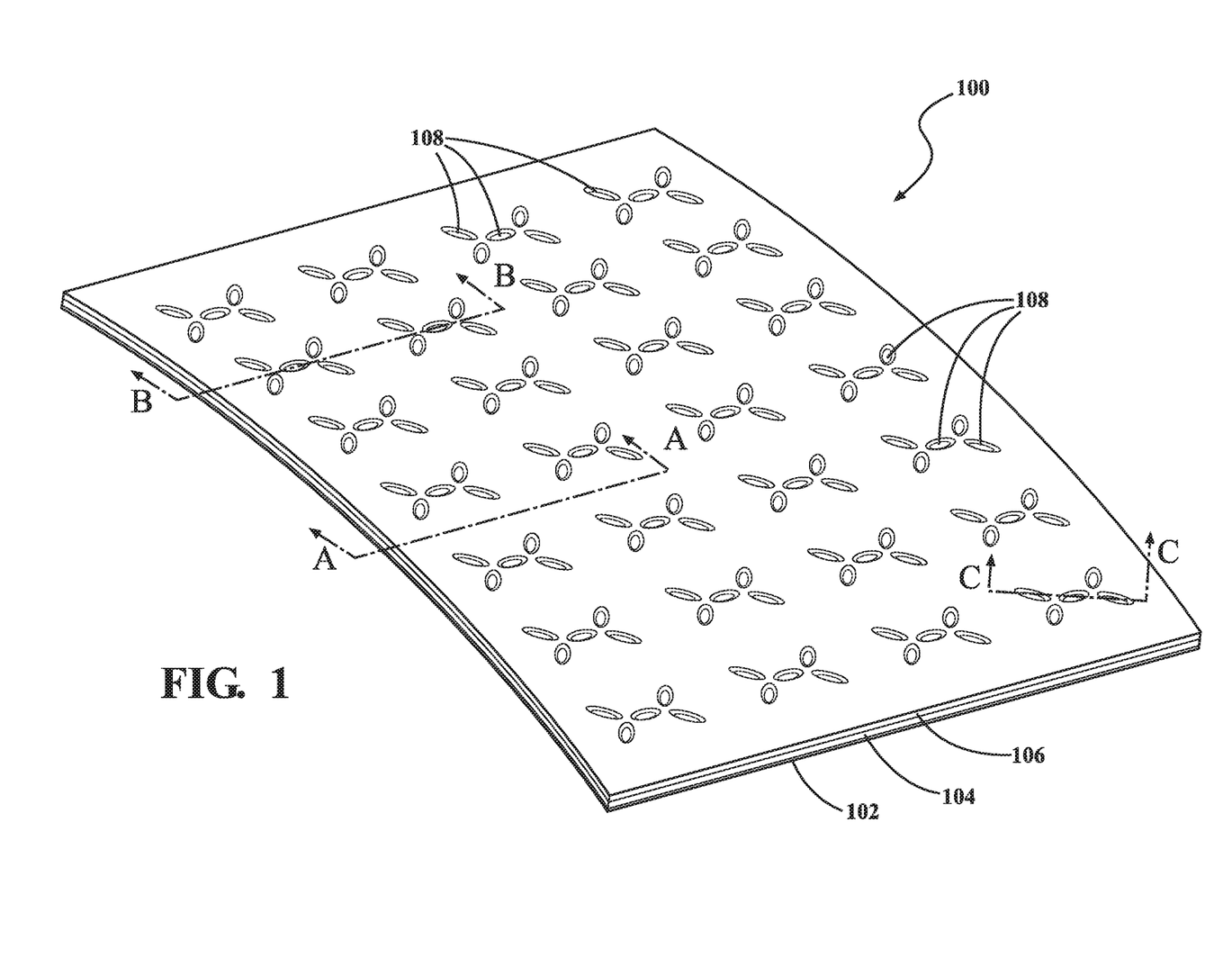
FIG. 1 is a top perspective view of an absorbent composite according to various embodiments of the disclosure.

As shown in FIG. 1, the present disclosure relates to an absorbent composite 100. The absorbent composite 100 may be of the kind which is intended for one-time use only and is disposable. The absorbent composite 100 includes a porous base layer 102, an absorbent core layer 104, and a superabsorbent laminate layer 106.

Each of the core layer 104 and the superabsorbent laminate layer 106 include superabsorbent polymers, at different concentrations, as detailed further hereinbelow. Superabsorbent polymers are cross-linked networks of flexible polymer chains. The most efficient water absorbers are polymer networks that carry dissociated ionic functional groups. As nonlimiting examples, the superabsorbent polymers of the present disclosure may include sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, made by gel polymerization, suspension polymerization or solution polymerization, and combinations thereof. Superabsorbent polymer works by diffusion on the molecular level. Water diffuses into the particles of superabsorbent polymer, and superabsorbent polymer particles swell to accommodate the additional water molecules. Because the polymer molecules are cross-linked, they do not dissolve in the absorbed liquid.

The base layer 102, the core layer 104, and the superabsorbent laminate layer 106 are compressed together. The superabsorbent laminate layer 106 is embossed to provide a plurality of embossed depressions 108 across a major surface area of the superabsorbent laminate layer 106. The embossed depressions 108 may have a multiaxial arrangement as shown in FIG. 1, and as also described further hereinbelow.

Figure 2:
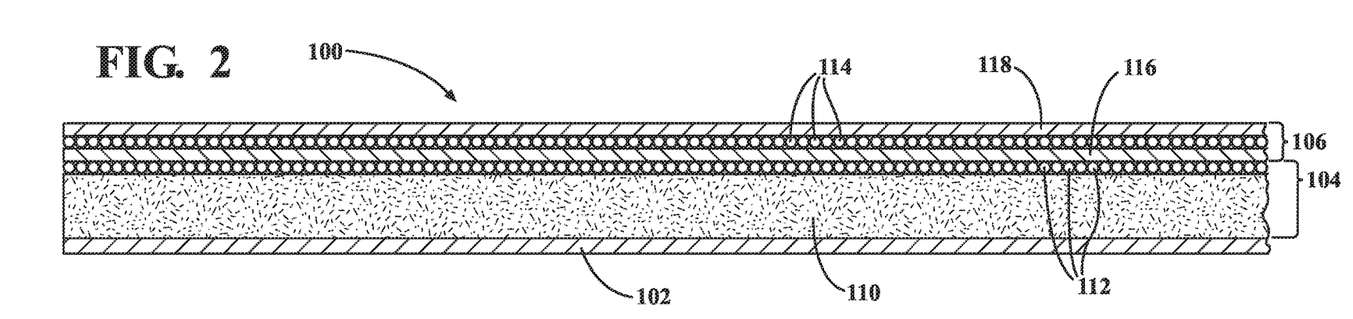
FIG. 2 is a cross-sectional side elevational view of the absorbent composite according to one embodiment of the disclosure and taken at section line A-A in FIG. 1.
Figure 3:
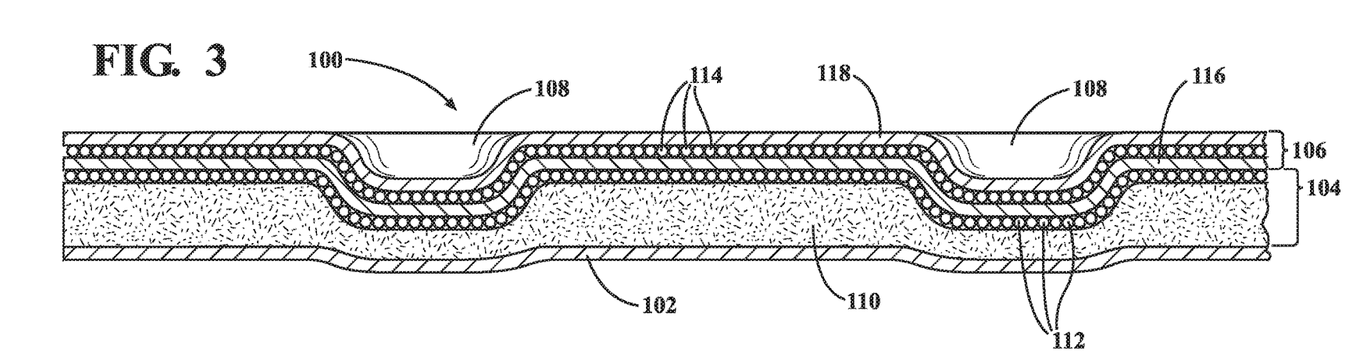
FIG. 3 is a cross-sectional side elevational view of the absorbent composite according to one embodiment of the disclosure and taken at section line B-B in FIG. 1.
Figure 4:
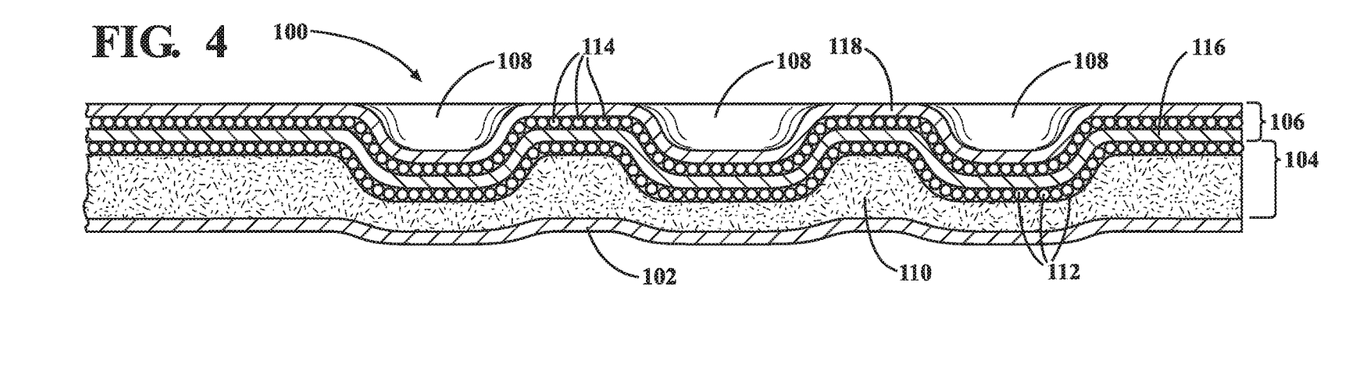
FIG. 4 is a cross-sectional side elevational view of the absorbent composite according to one embodiment of the disclosure and taken at section line C-C in FIG. 1.

The absorbent composite 100 according to one particular embodiment of the present disclosure is shown in FIGS. 2-4. The base layer 102 may serve as a first substrate during assembly of the absorbent composite 100, as described further herein, onto which the core layer 104 and the superabsorbent laminate layer 106 are laminated. The base layer 102 is porous to permit absorption and diffusion of blood, exudate, and other fluids when the absorbent composite 100 is used for wound care, for example.

The base layer 102 may be formed from a porous singleply cellulosic tissue, for example. However, one of ordinary skill in the art may also select other suitable materials for the porous tissue of the base layer 102, as desired.

Although the absorbent composite 100 is shown as having a single base layer 102, it should be understood that additional base or substrate layers may also be provided. The term "substrate layer" as used herein is defined as including any porous material suitable to form the absorbent composite 100 of the present disclosure, and may include cellulosic tissues, non-woven materials, and airlaid layers, as nonlimiting examples.

As also depicted in FIGS. 2-4, the core layer 104 is disposed adjacent to the base layer 102. The core layer 104 includes a fluff pulp layer 110. As one example, the fluff pulp layer 110 includes air formed or airlaid fluff formed by fiberizing cellulose sheets obtained from long fiber softwoods. However, other suitable application methods for forming the fluff pulp layer 110 of the core layer 104 may also be employed.

In certain examples, the fluff pulp layer 110 has between about 50 and about 150 grams per square meter of the fluff, more particularly between about 75 and about 125 grams per square meter of the fluff, and most particularly about 100 grams per square meter of the fluff. One of ordinary skill in the art may also select other suitable concentrations for the fluff in the fluff pulp layer 110, as desired.

Although the absorbent composite 100 is shown as having a single fluff pulp layer 110, it should be understood that additional fluff pulp layers may also be provided in order to selectively adjust a total softness of the absorbent composite 100.

In one example, the fluff pulp layer 110 is untreated, thereby making it particularly suitable for use in wound care bandages or dressings. However, a skilled artisan may also select a suitable treatment of the fluff pulp layer 110 of the core layer 104 such as medicaments, anti-bacterial agents, or buffering agents suitable for use in wound care bandages or dressings, within the scope of the present disclosure.

In addition to the use of fluff pulp 110, the core layer 104 also contains a first superabsorbent polymer layer 112. The first superabsorbent polymer layer 112 may include a discrete layer of superabsorbent polymer particles substantially evenly distributed atop the fluff layer 110, as illustrated in FIGS. 2-4. In particular, the first superabsorbent polymer layer 112 is disposed on a side of the fluff pulp layer 110 opposite the base layer 102.

In certain examples, the first superabsorbent polymer layer 112 has the superabsorbent polymer particles in an amount up to about 80 grams per square meter (gsm), more particularly between about 20 and about 60 grams per square meter, and most particularly about 40 grams per square meter. One of ordinary skill in the art may also select other suitable concentrations of the superabsorbent polymer particles in the first superabsorbent polymer layer 112, as desired.

As further shown in FIGS. 2-4, the superabsorbent laminate layer 106 of the present disclosure may be formed from at least one second superabsorbent polymer layer 114 that is sandwiched between at least one first substrate layer 116 and at least one second substrate layer 118. The second superabsorbent polymer layer 114 may include a discrete layer of superabsorbent polymer particles substantially evenly distributed between the first substrate layer 116 and the second substrate layer 118. The first substrate layer 116 and the second substrate layer 118 are porous. Each of the first substrate layer 116 and the second substrate layer 118 may be single-ply cellulosic tissues, for example. It should be appreciated that a skilled artisan may also select other suitable materials for the first substrate layer 116 and the second substrate layer 118 within the scope of the disclosure.

In certain examples, the second superabsorbent polymer layer 114 has the superabsorbent polymer particles in an amount up to about 300 grams per square meter, more particularly between about 100 and 200 grams per square meter, and most particularly about 150 grams per square meter. One of ordinary skill in the art may also select other suitable concentrations of the superabsorbent polymer particles in the second superabsorbent polymer layer 114, as desired.

Where the superabsorbent laminate layer 106 is formed in a single pass, with a single second superabsorbent polymer layer 114 sandwiched between a single first substrate layer 116 and a single second substrate layer 118, it should be appreciated that the superabsorbent laminate layer 106 may have a maximum concentration of about 200 gsm of the superabsorbent polymer particles. Where the superabsorbent laminate layer 106 is formed in two passes, there may be two second superabsorbent polymer layers 114, one of which is sandwiched between a single first substrate layer 116 and an inner issue layer (not shown), and another of which is sandwiched between the inner substrate layer and the single second substrate layer 116. In such an assembly, it should be appreciated that each of the superabsorbent polymer layers 114 may have about 150 gsm of the superabsorbent polymer particles, to provide for a total concentration of about 300 gsm of the superabsorbent polymer particles in the superabsorbent laminate layer 106. Other suitable laminated constructions for the superabsorbent laminate layer 106 and total concentrations of the superabsorbent polymer particles may also be used, and are considered within the scope of the present disclosure.

Taking into account the total amount of superabsorbent polymer particles in the first superabsorbent polymer layer 112 and the second superabsorbent polymer layer 114, it should be appreciated that the absorbent composite may have up to about 380 grams per square meter of the superabsorbent polymer particles, and more particularly between about 10 and about 380 grams per square meter, and most particularly about 380 grams per square meter. Other concentrations of the total amount of the superabsorbent polymer particles in the absorbent composite 100 may also be selected.

Although only the first superabsorbent polymer layer 112 and the second superabsorbent polymer layer 114 are shown in FIGS. 2-4 and described hereinabove, it should be understood that the absorbent composite 100 has a minimum of such layers. Other embodiments having more than two layers of superabsorbent polymer particles are also contemplated and considered within the scope of the present disclosure.

In an illustrative example, the superabsorbent laminate layer 106 may be pre-manufactured offline in the form of a Gelok® core, commercially available from Gelok International in Dunbridge, Ohio. The Gelok® core may be manufactured with or without adhesive between the first and second substrate layers 116, 118, as desired. Where no adhesive is employed, the tissues 116, 118 are secured and bonded to the second superabsorbent polymer layer 114 through an application of heat and pressure in the presence of water moisture. Without being bound to any particular theory, it is believed that the presence of water moisture, which may be provided in the form of a mist or spray, contributes to a hydrogen bonding between the superabsorbent polymer layer 114 and the tissues 116, 118, and may also facilitate a mechanical bonding by causing the superabsorbent polymer layer 114 to swell slightly and intermesh with the tissues 116, 118 under the application of the heat and pressure.

One particularly suitable Gelok® core may have product specifications as shown below in TABLE 1.

TABLE 1

Product specifications for Gelok ® core material.

|  | Standard Data | Metric Data |
| --- | --- | --- |
| Basis Wt: | 33.0 g/sq. ft | 355 g/sq. m. |
| Weight of Superabsorbent | 27.9 g/sq. ft. | 300 g/sq. m. |
| Thickness | 27.8 mils | 706 microns |
| Absorbency in 0.9% NaCl |  |  |
| 30 Sec: | 650 g/sq. ft. | 7000 g/sq. m. |
| 5 Min: | 1220 g/sq. ft. | 13130 g/sq. m. |
| MD Tensile | 2.9 lb/in. | 1.3 kg/in. |
| MD Elongation | 7.3% | 7.3% |
| Yield | 1.5 sq. yd/lb | 2.8 sq. m/kg |

Although it may be preferred to have the superabsorbent laminate layer 106 pre-manufactured offline, in alternative embodiments the superabsorbent laminate layer 106 may be manufactured online by suitable processes including airlaid, wetlaid and through air drying (TAD), as nonlimiting examples.

It should be further appreciated that the superabsorbent laminate layer 106, due to the sandwiching of a relatively high concentration of superabsorbent polymer particles in the second superabsorbent polymer layer 114 between the first and second substrate layers 116, 118, is ordinarily stiff or paperboard-like and limited in flexibility. Accordingly, the present disclosure further includes the provision of the embossed depressions 108 across the major surface area of the superabsorbent laminate layer 106, as shown in FIGS. 1-4. In addition to providing a mechanical bonding of the absorbent composite 100 at the embossed depressions 108, the embossed depressions 108 serve to break up a continuity of the superabsorbent laminate layer 106 and facilitate a greater flexibility and softness of the superabsorbent laminate layer 106 relative to its ordinary, non-embossed state.

With reference to FIGS. 3 and 4, for example, the embossing pattern penetrates through the entirety of the absorbent composite 100. This may form minor raised portions on the base layer 102 opposite the embossed depressions 108, or otherwise may form areas where the embossing is visually apparent on the base layer 102 due to the greater compression of the layers at the embossed depressions 108.

The concentration of the embossed depressions 108 across the surface area is also selected to optimize the flexibility and softness of the superabsorbent laminate layer 106. It has been surprising found that too little embossing does not sufficiently soften the superabsorbent laminate layer 106, and that too much embossing in fact causes the superabsorbent laminate layer 106 to be as stiff as the non-embossed state.

The embossing pattern selected for the absorbent composite 100 may also be multiaxial, so as to provide for enhanced flexibility along different angles relative to a longitudinal axis of the absorbent composite 100. For example, as shown in FIG. 3, the embossing pattern selected may provide the embossed depressions 108 along a first axis (shown in FIG. 1 by section line B-B) extending across a width of the absorbent composite 100 substantially orthogonal with a side edge of the absorbent composite 100. Furthermore, as shown in FIG. 4, the embossing pattern selected may also provide the embossed depressions 108 along a second axis (shown in FIG. 1 by section line C-C) that is transverse to the first axis extending across the width of the absorbent composite 100. Without being bound to any particular theory, it is believed that the multiaxial arrangement of the embossed depressions 108 extending through the entirety of the absorbent composite 100 advantageously contributes to a softness and pliability of the resulting absorbent composite 100 suitable for wound care bandages and dressings.

It should also be appreciated that the embossing acts to improve the handling, wicking and acquisition of the fluid, in operation. In particular, the embossing forms natural channels for the fluid to flow through, thereby improving the above-mentioned properties.

In certain examples, the absorbent composite 100 of the present disclosure may have a total thickness of between about 900 microns and about 1,500 microns, more particularly between about 1,000 microns and about 1,400 microns, and most particularly about 1,200 microns. One of ordinary skill in the art may select other suitable thicknesses for the absorbent composite 100, for example, depending the intended application such as wound care, feminine care, protective underwear, incontinence pads and liners, diapers, and food pads, as desired.

Figure 8:
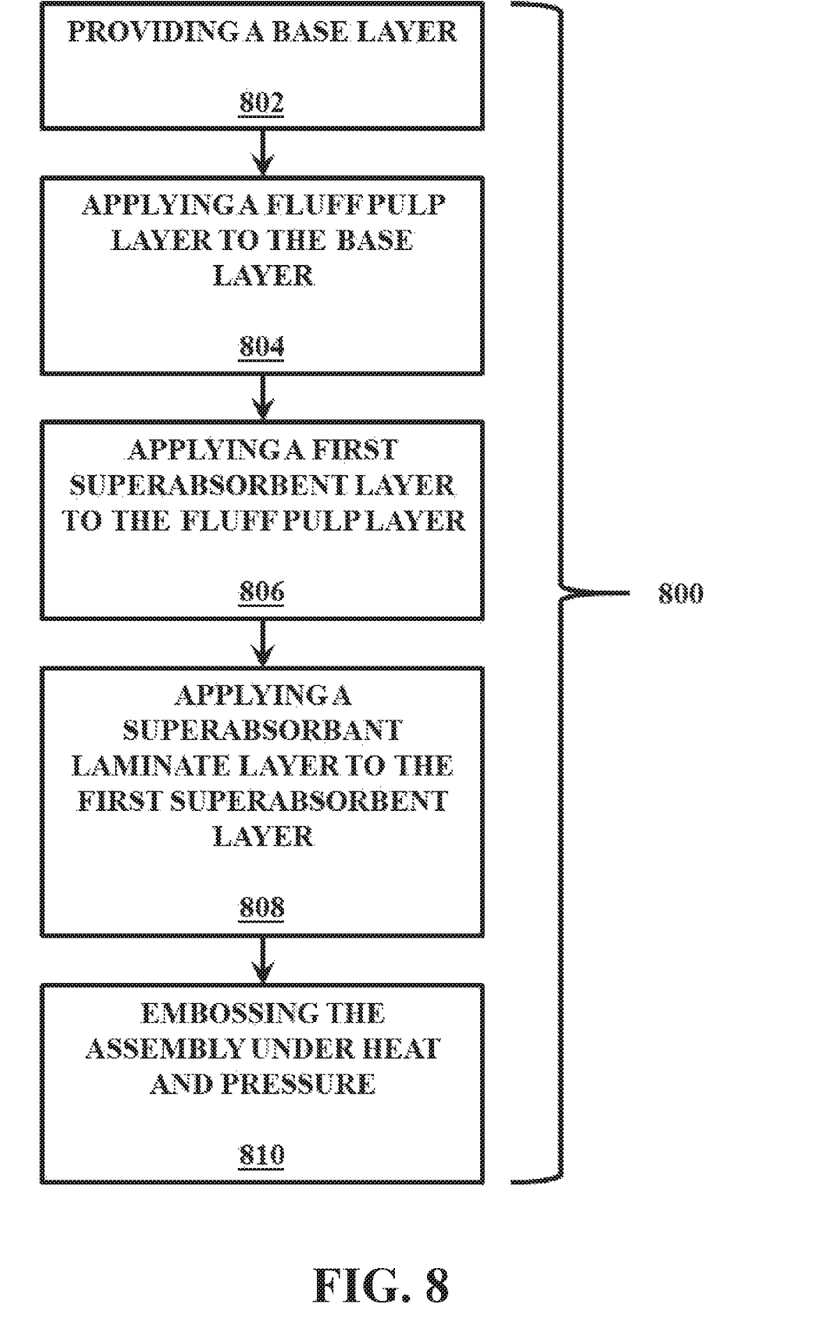
FIG. 8 is a flow diagram illustrating a method for manufacturing the absorbent composite as shown in FIGS. 2-4.

The present disclosure also includes a first method 800 of manufacturing the absorbent composite 100, as shown in FIG. 8. The method 800 includes a first step 802 of providing the base layer 102. In a second step 804, the fluff pulp layer 110 of the core layer 104 is then applied to the base layer 102, for example, by an air forming manufacturing process, in order to complete the core layer 104. In a third step 806, the first superabsorbent polymer layer 112 is then applied as the discrete layer atop the fluff pulp layer 110, for example, by a spraying or gravity-assisting deposition process. In a fourth step 808, the pre-manufactured superabsorbent laminate layer 106 is then applied to the core layer 104. The entire assembly is subsequently compressed together under heat and pressure, for example, through an embossing unit, to apply the embossed depressions 108 to the superabsorbent laminate layer 106 in a step 810. The absorbent composite 100 of the present disclosure is thereby secured and bonded together as a cohesive laminated assembly for end use.

Figure 5:
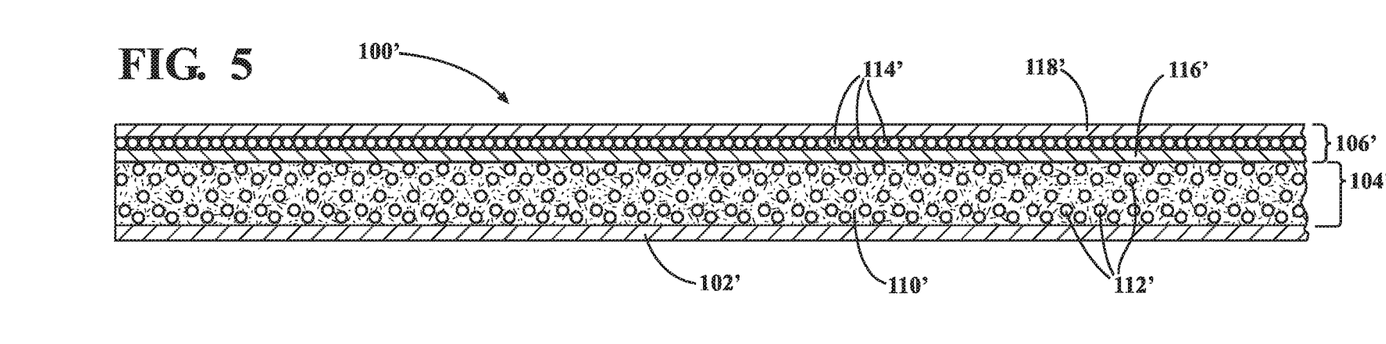
FIG. 5 is a cross-sectional side elevational view of the absorbent composite according to another embodiment of the disclosure and taken at section line A-A in FIG. 1.
Figure 6:
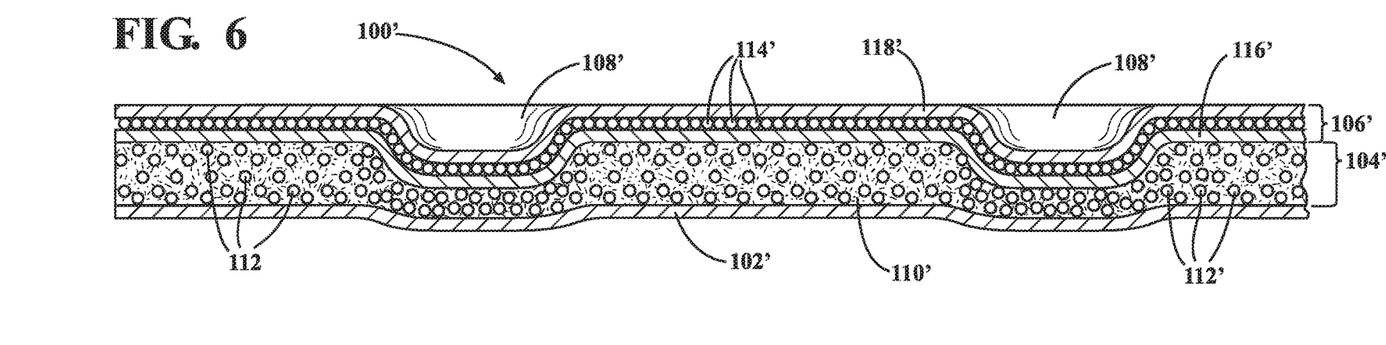
FIG. 6 is a cross-sectional side elevational view of the absorbent composite according to another embodiment of the disclosure and taken at section line B-B in FIG. 1.
Figure 7:
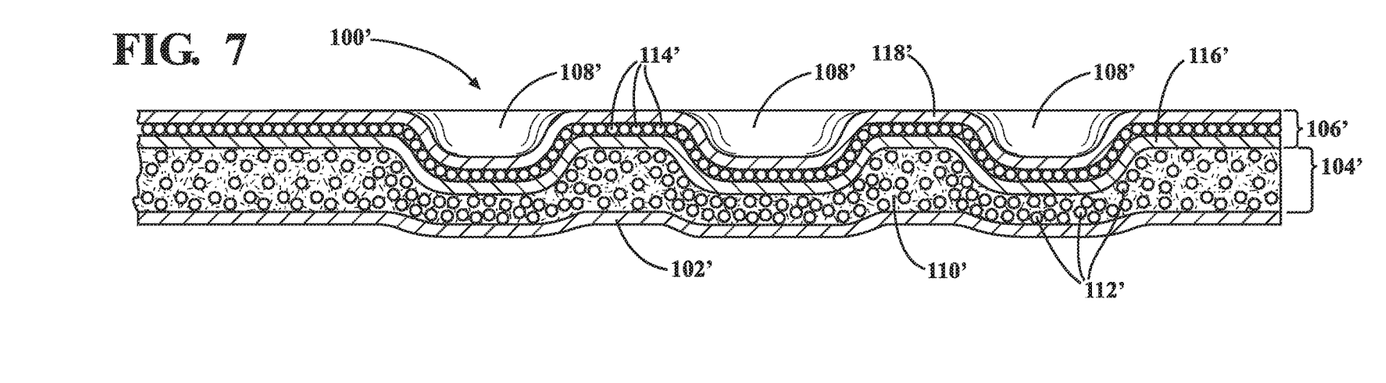
FIG. 7 is a cross-sectional side elevational view of the absorbent composite according to another embodiment of the disclosure and taken at section line C-C in FIG. 1.

The absorbent composite 100' according to an additional embodiment of the present disclosure is shown in FIGS. 5-7. Like or related structure to that shown in FIGS. 2-4 is depicted in FIGS. 5-7 with a prime symbol (') for the purpose of clarity.

The base layer 102', the core layer 104', and the superabsorbent laminate layer 106' are compressed together. The superabsorbent laminate layer 106' is embossed to provide a plurality of embossed depressions 108' across a major surface area of the superabsorbent laminate layer 106'. The embossed depressions 108' may have a multiaxial arrangement as shown in FIG. 1, and as also described further hereinbelow.

The base layer 102' of the absorbent composite 100' may serve as a first substrate during assembly of the absorbent composite 100', as described further herein, onto which the core layer 104' and the superabsorbent laminate layer 106' are laminated. The base layer 102' is porous to permit absorption and diffusion of blood, exudate, and other fluids when the absorbent composite 100' is used for wound care, for example.

The base layer 102' may be formed from a porous single-ply cellulosic tissue, for example. However, one of ordinary skill in the art may also select other suitable materials for the porous tissue of the base layer 102', as desired.

Although the absorbent composite 100' is shown as having a single base layer 102', it should be understood that additional base or substrate layers may also be provided. The term "substrate layer" as used herein is defined as including any porous material suitable to form the absorbent composite 100' of the present disclosure, and may include cellulosic tissues, non-woven materials, and airlaid layers, as non-limiting examples.

As also depicted in FIGS. 5-7, the core layer 104' is disposed adjacent to the base layer 102'. The core layer 104' includes a fluff pulp layer 110'. As one example, the fluff pulp layer 110' includes air formed fluff formed by fiberizing cellulose sheets obtained from long fiber softwoods. However, other suitable application methods for forming the fluff pulp layer 110' of the core layer 104' may also be employed.

In certain examples, the fluff pulp layer 110' has between about 50 and about 150 grams per square meter of the fluff, more particularly between about 75 and about 125 grams per square meter of the fluff, and most particularly about 100 grams per square meter of the fluff. One of ordinary skill in the art may also select other suitable concentrations for the fluff in the fluff pulp layer 110', as desired.

Although the absorbent composite 100' is shown as having a single fluff pulp layer 110', it should be understood that additional fluff pulp layers may also be provided in order to selectively adjust a total softness of the absorbent composite 100'.

In one example, the fluff pulp layer 110' is untreated, thereby making it particularly suitable for use in wound care bandages or dressings. However, a skilled artisan may also select a suitable treatment of the fluff pulp layer 110' of the core layer 104' such as medicaments, anti-bacterial agents, or buffering agents suitable for wound care bandages or dressings, within the scope of the present disclosure.

In addition to the use of fluff pulp 110', the core layer 104' also contains first superabsorbent polymer particles 112'. Unlike the embodiment shown in FIGS. 2-4, the first superabsorbent polymer particles 112' are dispersed throughout the fluff pulp layer 110' as illustrated in FIGS. 5-7. In other words, the embodiment shown in FIGS. 5-7 intermixes the first superabsorbent polymer particles 112' with the fluff pulp layer 110', instead of providing the superabsorbent polymer particles 112' as a discrete layer adjacent to the fluff pulp layer 110'.

In certain examples, the fluff pulp layer 110' has the first superabsorbent polymer particles 112' in an amount up to about 80 grams per square meter, more particularly between about 20 and about 60 grams per square meter, and most particularly about 40 grams per square meter. One of ordinary skill in the art may also select other suitable concentrations of the superabsorbent polymer particles 112' in the fluff pulp layer 110' forming the core layer 104', as desired.

As further shown in FIGS. 5-7, the superabsorbent laminate layer 106' of the present disclosure may be formed from a second superabsorbent polymer layer 114' that is sandwiched between a first substrate layer 116' and a second substrate layer 118'. The second superabsorbent polymer layer 114' may include a discrete layer of superabsorbent polymer particles substantially evenly distributed between the first substrate layer 116' and the second substrate layer 118'. The first substrate layer 116' and the second substrate layer 118' are porous. Each of the first substrate layer 116' and the second substrate layer 118' may be single-ply cellulosic tissues, for example. It should be appreciated that a skilled artisan may also select other suitable materials for the first substrate layer 116' and the second substrate layer 118' within the scope of the disclosure.

In certain examples, the second superabsorbent polymer layer 114' has the superabsorbent polymer particles in an amount up to about 300 grams per square meter, more particularly between about 100 and 200 grams per square meter, and most particularly about 150 grams per square meter. One of ordinary skill in the art may also select other suitable concentrations of the superabsorbent polymer particles in the second superabsorbent polymer layer 114', as desired.

Where the superabsorbent laminate layer 106' is formed in a single pass, with a single second superabsorbent polymer layer 114' sandwiched between a single first substrate layer 116' and a single second substrate layer 118', it should be appreciated that the superabsorbent laminate layer 106' may have a maximum concentration of about 200 gsm of the superabsorbent polymer particles. Where the superabsorbent laminate layer 106' is formed in two passes, there may be two second superabsorbent polymer layers 114', one of which is sandwiched between a single first substrate layer 116' and an inner issue layer (not shown), and another of which is sandwiched between the inner substrate layer and the single second substrate layer 116'. In such an assembly, it should be appreciated that each of the superabsorbent polymer layers 114' may have about 150 gsm of the superabsorbent polymer particles, to provide for a total concentration of about 300 gsm of the superabsorbent polymer particles in the superabsorbent laminate layer 106'. Other suitable laminated constructions for the superabsorbent laminate layer 106' and total concentrations of the superabsorbent polymer particles may also be used, and are considered within the scope of the present disclosure.

Taking into account the total amount of superabsorbent polymer particles in the first superabsorbent polymer layer 112' and the second superabsorbent polymer layer 114', it should be appreciated that the absorbent composite may have up to about 380 grams per square meter of the superabsorbent polymer particles, and more particularly between about 10 and about 380 grams per square meter, and most particularly about 380 grams per square meter. Other concentrations of the total amount of the superabsorbent polymer particles in the absorbent composite 100' may also be selected.

Although only the first superabsorbent polymer particles 112' intermixed in the fluff pulp layer 110' and the superabsorbent polymer particles of the second superabsorbent polymer layer 114' are shown in FIGS. 5-7, and described hereinabove, it should be understood that the absorbent composite 100' has a minimum of such layers. Other embodiments having more than two layers containing superabsorbent polymer particles are also contemplated and considered within the scope of the present disclosure.

In an illustrative example, the superabsorbent laminate layer 106' may be pre-manufactured offline in the form of a Gelok® core, as described hereinabove and detailed in TABLE 1.

Although it may be preferred to have the superabsorbent laminate layer 106' pre-manufactured offline, in alternative embodiments the superabsorbent laminate layer 106' may be manufactured online by suitable processes including airlaid, wetlaid and through air drying (TAD), as nonlimiting examples.

It should be further appreciated that the superabsorbent laminate layer 106', due to the sandwiching of a relatively high concentration of superabsorbent polymer particles in the second superabsorbent polymer layer 114' between the first and second substrate layers 116', 118' is ordinarily stiff or paperboard-like in flexibility. Accordingly, the present disclosure further includes the provision of the embossed depressions 108' across the major surface of the superabsorbent laminate layer 106', as shown in FIG. 1 and FIGS. 5-7. In addition to providing a mechanical bonding of the absorbent composite 100' at the embossed depressions 108', the embossed depressions 108' serve to break up a continuity of the superabsorbent laminate layer 106' and facilitate a greater flexibility and softness of the superabsorbent laminate layer 106' relative to its ordinary state.

It should also be appreciated the embossed depressions 108' may further serve to compress and make more concentrated the superabsorbent polymer particles 112' in the underlying core layer 104' in the regions of the core layer 104' immediately beneath the embossed depressions 108', relative to the regions of the core layer 104' between the embossed depressions 108', as shown in FIGS. 6 and 7. Advantageously, this may slow absorption of fluid at the embossed depressions 108', and encourage a distribution of fluid to the regions between the embossed depressions 108', in operation.

With reference to FIGS. 6 and 7, for example, the embossing pattern penetrates through the entirety of the absorbent composite 100'. This may form minor raised portions on the base layer 102' opposite the embossed depressions 108', or otherwise may form areas where the embossing is visually apparent on the base layer 102' due to the greater compressions of the layers under the embossed depressions 108'.

The concentration of the embossed depressions 108' across the surface area is also selected to optimize the flexibility and softness of the superabsorbent laminate layer 106'. It has been surprising found that too little embossing does not sufficiently soften the superabsorbent laminate layer 106', and that too much embossing in fact causes the superabsorbent laminate layer 106' to be as stiff as the non-embossed state.

The embossing pattern selected for the absorbent composite 100' may also be multiaxial, so as to provide for enhanced flexibility along different angles relative to a longitudinal axis of the absorbent composite 100'. For example, as shown in FIG. 6, the embossing pattern selected may provide the embossed depressions 108' along a first axis (shown in FIG. 1 by section line B-B) extending across a width of the absorbent composite 100' substantially orthogonal with a side edge of the absorbent composite 100'. Furthermore, as shown in FIG. 4, the embossing pattern selected may also provide the embossed depressions 108' along a second axis (shown in FIG. 1 by section line C-C) that is transverse to the first axis extending across the width of the absorbent composite 100'. Without being bound to any particular theory, it is believed that the multiaxial arrangement of the embossed depressions 108' extending through the entirety of the absorbent composite 100' advantageously contributes to a softness and pliability of the resulting absorbent composite 100' suitable for wound care bandages and dressings.

It should also be appreciated that the embossing acts to improve the handling, wicking and acquisition of the fluid, in operation. In particular, the embossing forms natural channels for the fluid to flow through, thereby improving the above-mentioned properties.

In certain examples, the absorbent composite 100' of the present disclosure may have a total thickness of between about 900 microns and about 1,500 microns, more particularly between about 1000 microns and about 1400 microns, and most particularly about 1200 microns. One of ordinary skill in the art may select other suitable thicknesses for the absorbent composite 100', for example, depending the intended application such as wound care, feminine care, protective underwear, incontinence pads and liners, diapers, and food pads, as desired.

Figure 9:
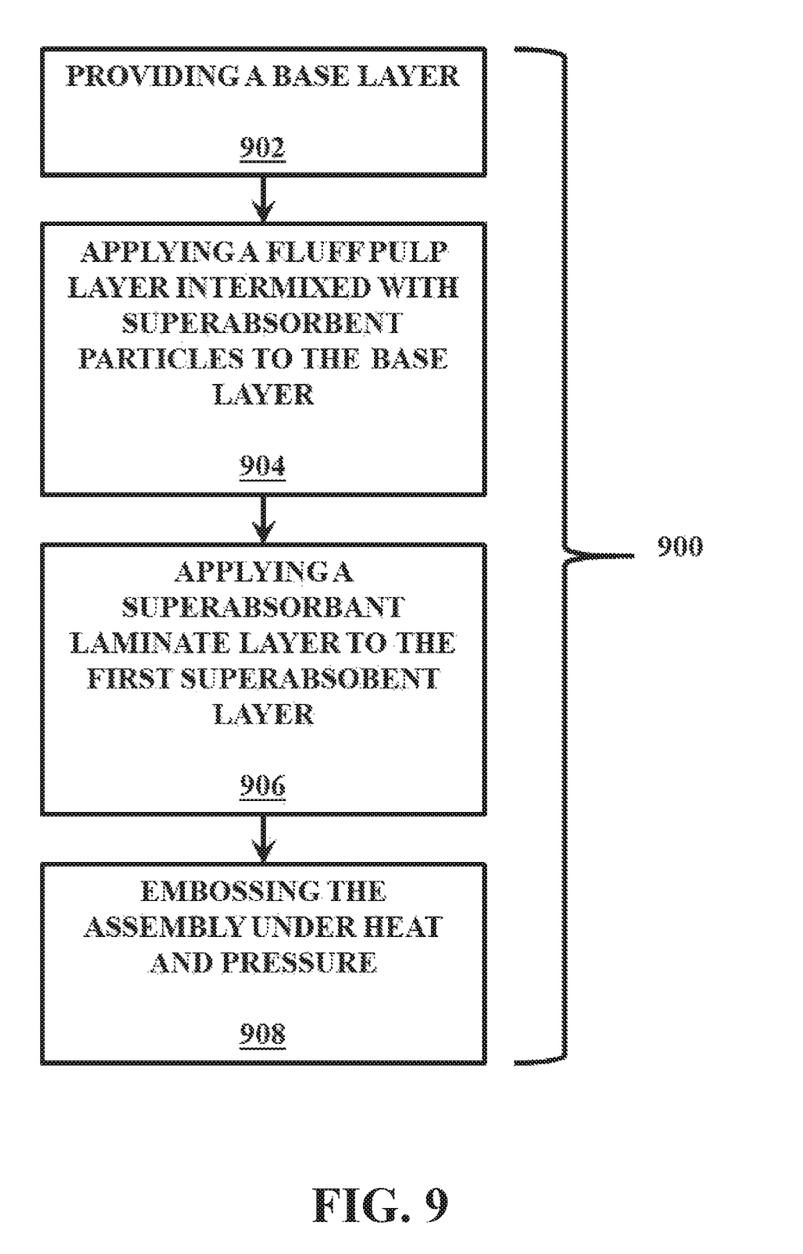
FIG. 9 is a flow diagram illustrating a method for manufacturing the absorbent composite as shown in FIGS. 5-7.

The present disclosure also includes a second method 900 of manufacturing the absorbent composite 100', as shown in FIG. 9. The method 900 includes a first step 902 of providing the base layer 102. In a second step 904, the fluff pulp layer 110' intermixed with the superabsorbent polymer particles 112' and defining the core layer 104' is then applied to the base layer 102', for example, by an air forming manufacturing process. In a third step 906, the pre-manufactured superabsorbent laminate layer 106' is then applied to the core layer 104'. The entire assembly is subsequently compressed together under heat and pressure, for example, through an embossing unit, to apply the embossed depressions 108' to the superabsorbent laminate layer 106' in a step 908. The absorbent composite 100' of the present disclosure is thereby secured and bonded together as a cohesive laminated assembly for end use.

It should be appreciated that in both methods 800 and 900 described hereinabove, the embossing unit is heated and pressurized, allowing for two different forms of bonding, ensuring integrity of the ultimate absorbent composite 100, 100'. The heat and pressure cause a hydrogen bond of water, either found naturally in the composite layer or added by spray or mist during the methods 800, 900, while the penetration of embossing points causes a mechanical bond throughout the absorbent composite 100, 100'. These two forms of bonding ensure overall integrity of the absorbent composite 100, 100' throughout manufacturing and converting.

In a preferred embodiment, the superabsorbent laminate layer 106, 106' will be produced off line, for example, at another manufacturing facility. The air formed core layer 104, 104' will be formed on line following conventional air forming manufacturing techniques, and the two parts will be processed through the heated and pressurized embossing unit with the unique embossing pattern described hereinabove to manufacture the absorbent composite 100, 100'.

During manufacturing of a finished absorbent composite 100, 100' according to the methods 800, 900, such as for a wound care dressing, the absorbent composite 100, 100' will be rotated to place the superabsorbent laminate layer 106, 106' as the bottom-most substrate, for example, for packaging purposes and end use, thereby providing the base layer 102, 102' and the core layer 104, 104' as the top-most substrate. By using this orientation, it should be appreciated that the overall softness and pliability of the absorbent composite 100, 100' will be optimized. By using the superabsorbent laminate layer 106, 106' as the bottom-most layer of the overall absorbent composite 100, 100', the superabsorbent laminate layer 106, 106' will perform as a wicking layer and fluid reservoir to ensure dryness of the patient and optimal absorbency of the entire absorbent composite 100, 100'.

Examples

Exemplary product measurements for absorbent composites manufactured according to the above-described methods are shown below in TABLES 2 and 3.

TABLE 2

Measurements for the assembled base layer and core layer of the absorbent composite prior to application of the superabsorbent laminate layer.

| Composition | |
|---|---|
| Pulp (g/m$^2$) | 70 |
| Superabsorbent (g/m$^2$) | 46 |
| Tissue (g/m$^2$) | 34 |
| Specification | |
| Basis Weight (g/m$^2$) | 150 |
| Thickness (microns) | 745 |

The example shown in TABLE 2 is the simplest form the absorbent composite described hereinabove, with a single cellulosic base layer, a fluff layer with intermixed superabsorbent particles, and a simple cellulosic top layer without the superabsorbent laminate layer having been applied.

TABLE 3

Measurements for the assembled absorbent composite according to one embodiment.

| Composition | |
|---|---|
| Pulp (g/m$^2$) | 70 |
| Superabsorbent (g/m$^2$) | 300 |
| Tissue (g/m$^2$) | 75 |
| Specification | |
| Basis Weight (g/m$^2$) | 445 |
| Thickness (microns) | 1113 |
| Absorption Capacity (g/m$^2$) | 15410 |
| Density (g/cm$^3$) | 0.23 |
| Absorption Capacity (g/m$^2$) | 3710 |

The example shown in TABLE 3 is the form the absorbent composite 100' described hereinabove, with a single cellulosic base layer, a fluff layer without intermixed superabsorbent particles, and a superabsorbent laminate layer having been applied. The superabsorbent laminate layer in this case has three cellulosic substrate layers, and two layers of 150 gsm superabsorbent polymer particles (i.e., a cellulosic substrate layer/150 gsm of SAP/cellulosic substrate layer/150 gsm of SAP/cellulosic substrate layer; 3 substrates, 2 SAP layers in the laminate layer).

Advantageously, the absorbent composite 100, 100' of the present disclosure allows for the unique feature of a highly compressed, ultra-thin product capable of absorbing large amounts of fluid without gel-blocking. The absorbent composite 100, 100' furthermore achieves low rewets due to a lack of un-absorbed fluids and has excellent fluid acquisition and wicking performance. Each of these attributes is critical to disposable wound care markets as well as others such as feminine care, protective underwear, incontinence pads and liners, diapers, and food pads.

While certain representative embodiments and details have been shown for purposes of illustrating the invention, it will be apparent to those skilled in the art that various changes may be made without departing from the scope of the disclosure, which is further described in the following appended claims.

What is claimed is:

1. An absorbent composite, comprising:
a porous base layer;
an absorbent core layer having a fluff pulp layer and superabsorbent polymer particles, the core layer disposed on the base layer; and
a superabsorbent laminate layer disposed on the core layer,
wherein the base layer, the core layer, and the superabsorbent laminate layer are compressed together to form a main body having a side edge, and embossed under heat and pressure to form a plurality of embossed depressions arranged across a major surface area of the superabsorbent laminate layer, the embossed depressions extending through the main body from the superabsorbent laminate layer and into the core layer and the base layer,
wherein each of the plurality of embossed depressions is spaced apart from a remainder of the embossed depressions,
wherein each of the embossed depressions is oval-shaped and has a length that is greater than a width; and
wherein the embossed depressions are arranged in a multiaxial embossed pattern, the multiaxial embossed pattern providing the embossed depressions disposed along a first axis and a second axis, the first axis extending across a width of the main body substantially orthogonal with the side edge of the main body and the second axis oriented transverse to the first axis.

2. The absorbent composite of claim 1, wherein the porous base layer is single-ply cellulosic tissue.

3. The absorbent composite of claim 1, wherein the superabsorbent polymer particles of the core layer are provided as a discrete first superabsorbent polymer layer disposed on the fluff pulp layer.

4. The absorbent composite of claim 1, wherein the superabsorbent polymer particles of the core layer are distributed through the fluff pulp layer.

5. The absorbent composite of claim 1, wherein the superabsorbent polymer particles of the core layer are present in an amount up to about 80 grams per square meter.

6. The absorbent composite of claim 3, wherein the superabsorbent laminate layer includes a second superabsorbent polymer layer sandwiched between a first substrate layer and a second substrate layer.

7. The absorbent composite of claim 6, wherein the second superabsorbent polymer layer contains superabsorbent polymer particles in an amount up to about 300 grams per square meter.

8. The absorbent composite of claim 1, having a total thickness of between about 900 microns and about 1,500 microns.

9. The absorbent composite of claim 1, further comprising additional superabsorbent polymer particles in the superabsorbent laminate layer, wherein the superabsorbent polymer particles of the core layer and the additional superabsorbent polymer particles of the superabsorbent laminate layer are present in a total amount of between about 10 grams per square meter and 380 grams per square meter.

10. The absorbent composite of claim 1, wherein the porous base layer, the core layer, and the superabsorbent laminate layer contain no adhesives.

11. A wound care bandage or dressing comprising the absorbent composite of claim 1.

12. A wound care bandage or dressing, comprising:
an absorbent composite including
a porous base layer of single-ply cellulosic tissue;
an absorbent core layer having a fluff pulp layer and superabsorbent polymer particles, the core layer disposed on the base layer, wherein the superabsorbent polymer particles are either disposed on the fluff pulp layer as a discrete first superabsorbent layer or distributed throughout the fluff pulp layer, the superabsorbent polymer particles present in the core layer in an amount up to about 80 grams per square meter; and
a superabsorbent laminate layer disposed on the core layer, wherein the superabsorbent laminate layer includes a second superabsorbent polymer layer sandwiched between a first substrate layer and a second substrate layer, and the second superabsorbent polymer layer contains superabsorbent polymer particles in an amount up to about 300 grams per square meter,
the porous base layer, the core layer, and the superabsorbent laminate layer containing no adhesives, and
the base layer, the core layer, and the superabsorbent laminate layer being compressed together to form a main body having a side edge, and embossed under heat and pressure to form a plurality of embossed depressions arranged across a major surface area of the superabsorbent laminate layer, each of the plurality of embossed depressions is spaced apart from a remainder of the embossed depressions, the embossed depressions extending through the main body from the superabsorbent laminate layer and into the core layer and the base layer, wherein the embossed depressions are arranged in a multiaxial embossed pattern, the multiaxial embossed pattern providing the embossed depressions disposed along a first axis and a second axis, the first axis extending across a width of the main body substantially orthogonal with the side edge of the main body and the second axis oriented transverse to the first axis,
wherein each of the embossed depressions is oval-shaped and has a length that is greater than a width,
wherein the main body has a total thickness of between about 900 microns and about 1,500 microns.

13. A method for manufacturing an absorbent composite, comprising:
providing a porous base layer;
applying a fluff pulp layer to the base layer to form an absorbent core layer, the core layer also including superabsorbent polymer particles;
applying a superabsorbent laminate layer on the core layer;
compressing the base layer, the core layer, and the superabsorbent laminate layer together under heat and pressure to form a main body having a side edge, and
embossing the main body to form a plurality of embossed depressions arranged across a major surface area of the superabsorbent laminate layer, each of the plurality of embossed depressions is spaced apart from a remainder of the embossed depressions, the embossed depressions extending through the main body from the superabsorbent laminate layer and into the core layer and the base layer, wherein the embossed depressions are arranged in a multiaxial embossed pattern, the multiaxial embossed pattern providing the embossed depressions disposed along a first axis and a second axis, the first axis extending across a width of the main body substantially orthogonal with the side edge of the main body and the second axis oriented transverse to the first axis, wherein each of the embossed depressions is oval-shaped and has a length that is greater than a width.

14. The method of claim 13, wherein the superabsorbent polymer particles of the core layer are providing by a step of applying a discrete first superabsorbent layer to the fluff pulp layer prior to the step of applying the superabsorbent laminate layer on the core layer.

15. The method of claim 13, wherein the superabsorbent polymer particles of the core layer are providing by a step of intermixing the superabsorbent polymer particles with fluff pulp of the fluff pulp layer either prior to or during the step of application the fluff pulp layer to the base layer.

16. The method of claim 13, further comprising a step of rotating the composite to place the superabsorbent laminate layer on the bottom for packaging and end use.

17. The method of claim 13, wherein the porous base layer, the core layer, and the superabsorbent laminate layer contain no adhesives, and the step of compressing the base layer, the core layer, and the superabsorbent laminate layer together under heat and pressure includes a step of spraying or misting water onto at least one of the base layer, the core layer, and the superabsorbent laminate layer to facilitate a laminating of the composite.

18. The absorbent composite of claim 1, wherein the embossed depressions include a first set of embossed depressions and a second set of embossed depressions, the length of each of the embossed depressions of the first set being oriented along the first axis, and the length of each of the embossed depressions of the second set being oriented along the second axis.

19. The absorbent composite of claim 1, wherein the superabsorbent laminate layer is disposed on an entirety of the core layer.

* * * * *